United States Patent [19]

Rheinish et al.

[11] Patent Number: 5,306,297
[45] Date of Patent: Apr. 26, 1994

[54] INTRAOCULAR LENS HAPTIC WITH ENLARGED ANCHORING HEAD

[75] Inventors: Robert S. Rheinish, Huntington Beach; Allan R. Tonks, Fontana; Thomas P. Richards, Los Angeles, all of Calif.

[73] Assignee: Kabi Pharmacia Ophthalmics, Inc., Monrovia, Calif.

[21] Appl. No.: 909,167

[22] Filed: Jul. 6, 1992

[51] Int. Cl.$^5$ .................................................. A61F 2/16
[52] U.S. Cl. ................................................................ 623/6
[58] Field of Search ................................................. 623/6

[56] References Cited

U.S. PATENT DOCUMENTS

| | | | |
|---|---|---|---|
| 4,242,760 | 1/1981 | Rainin | 623/6 |
| 4,315,337 | 2/1982 | Choyce | 623/6 |
| 4,439,873 | 4/1984 | Poler | 623/6 |
| 4,615,701 | 10/1986 | Woods | 623/6 |
| 4,617,023 | 10/1986 | Peyman | 623/6 |
| 4,790,846 | 12/1988 | Christ et al. | 623/6 |
| 4,880,426 | 11/1989 | Ting et al. | 623/6 |
| 4,888,013 | 12/1989 | Ting et al. | 623/6 |
| 4,894,062 | 1/1990 | Knight et al. | 623/6 |
| 4,938,767 | 7/1990 | Ting et al. | 623/6 |
| 4,961,746 | 10/1990 | Lim et al. | 623/6 |
| 4,964,206 | 10/1990 | Knoll et al. | 29/424 |
| 4,978,354 | 12/1990 | Van Gent | 623/6 |
| 4,995,879 | 2/1991 | Dougherty | 623/6 |
| 5,007,928 | 4/1991 | Okamura et al. | 623/6 |
| 5,141,507 | 8/1992 | Parekh | 623/6 |

*Primary Examiner*—Randy C. Shay
*Attorney, Agent, or Firm*—Poms, Smith, Lande & Rose

[57] ABSTRACT

The present invention provides an improved intraocular lens haptic having an enlarged anchoring head and an integrally formed support portion extending therefrom. An oblong hole is provided in the anchoring head. The haptic is punched from a sheet or ribbon of polyvinylidene fluoride film, and thereafter a lens optic is cast around the anchoring head. During the casting operation, the lens optic material fills in the oblong hole and all spaces around the anchoring head. Thus, the anchoring head is firmly embedded in an outer periphery of the lens optic. Because the haptic is punched, it can be fabricated to have a variety of different anchoring head shapes and to have a variety of support portion shapes with varying numbers of bends at different bend angles. The orientation of the oblong hole within the anchoring head is also easily changed as is the orientation of the anchoring head relative to the support portion, although both structures are integral and formed from a single sheet of material.

22 Claims, 1 Drawing Sheet

INTRAOCULAR LENS HAPTIC WITH ENLARGED ANCHORING HEAD

FIELD OF THE INVENTION

The present invention relates to support structures for intraocular lenses. More specifically, the present invention relates to an intraocular lens haptic having an oblong hole disposed in a unique enlarged anchoring head, wherein the haptic exhibits improved pull strength and stability.

BACKGROUND OF THE INVENTION

An intraocular lens has a principal refractive structure, known as a lens optic, and one or more support structures for positioning and centering the lens optic within the anterior or posterior chamber of an eye. Commonly referred to as "haptics", these support structures may be integrally formed with the lens optic (a one-piece lens), or separately manufactured and attached to the lens optic (a multi-piece lens).

An important goal for intraocular lens design is to minimize trauma to the eye when the lens is inserted. To that end, effort is made to ensure, for example, that the incision to the eye is kept small during the implantation operation; that biologically inert materials are used in the construction of the intraocular lens; and that the physical proportions of the lens do not interfere, irritate, or damage delicate inner eye tissue.

What makes achieving the design goals difficult is that often the characteristics necessary for a good lens optic are undesireable for the lens haptic, and vice versa. The two have conflicting design requirements.

Conventional intraocular lens optics, for instance, are commonly made from biocompatible materials such as polymethylmethacrylate (PMMA). With this rather rigid material, lens optics are easily cast or machined into their final form. So in regard to handling ease and manufacturability, the benefits of PMMA are obvious. By the same token, because this material is rigid, many of the foregoing design goals are compromised.

More recently, however, more flexible materials have been devised for the lens optic. Flexible lens optics cast of elastomeric materials such as silicone or hydrogels, for example, have gained popularity because they produce foldable intraocular lenses that may be inserted through a beneficially small incision in the eye.

Once the intraocular lens is implanted, the haptics must hold the lens optic in proper alignment with the optical axis of the eye as well as support the weight of the lens optic. The haptics must therefore be sufficiently rigid to perform their function. In short, haptics must simultaneously be pliant enough to avoid damaging delicate eye tissue yet rigid enough to act as a support structure.

To be sure, the majority of the so called "small incision lenses" have been limited to multi-piece designs. One reason is that a small incision lens connotes a flexible lens that is folded during implantation. Experience has seen that a flexible lens optic material that is desirable for the optic is usually too flimsy to work for the haptic in its support function—hence, the evolution toward the multi-piece lens design.

The type of material is also an issue. Elastomerics commonly used for the optic do not perform satisfactorily as a haptic, except in a broad flange configuration, which is less desirable than other more streamlined configurations. As a result, flexible intraocular lenses depend on more rigid polypropylene monofilament haptics.

A wide variety of haptic configurations intended for use with silicone or other elastomeric lens optics have been produced by permanent deformation of an elongated filament, as disclosed in U.S. Pat. No. 4,880,426 to Ting et al.; or by staking in the lens optic an anchor formed at an end of the filament haptic, as taught in U.S. Pat. No. 4,894,062 to Knight et al. Unfortunately, the Ting and Knight intraocular lenses exhibit only moderately satisfactory pull strengths. As is known in the art, pull strength is a measure of the haptic's ability to resist detachment from the lens optic when subjected to an outward, radial tensile force. Such a force, among others, is commonplace during implantation surgery.

In order to obtain acceptable pull strengths, some filament haptics are provided with an enlarged anchoring head that helps secure it to a flexible lens optic. But an enlarged anchoring head is usually difficult to form consistently because conventional manufacturing techniques involve, for example, winding an end of the monofilament material around a small diameter mandrel and ultrasonically welding the overlapping part of the filament to fix the looped shape. This technique is generally disclosed in U.S. Pat. No. 4,790,846 to Christ et al. The welding is necessary because without it, the loop cannot hold its form. Once the shape collapses, it is easy for the haptic to detach from the lens optic. Additionally, even if the loop were welded closed, the filament may be too flexible to retain the loop shape under tension, and again the loop would collapse.

Although the prior art looped-shape anchoring head helps interlock the haptic to the lens optic, and the design has met with some commercial success, it does have drawbacks. The process steps undergone in creating the looped anchoring head are extremely labor intensive, and require highly-trained technicians to skillfully guide intricate tools while observing through a magnifying lens. As such, it is difficult to maintain consistently high quality in the finished product. Also, because so much labor is involved, high production speeds cannot be attained. Consequently, conventional intraocular lenses of this type are not easily adapted to automated mass production, and production costs are significant.

Furthermore, by wrapping an end of the filament around the mandrel and welding it to create the closed loop, a double thickness of haptic material at the point of overlap is made. This double thickness may be greater than the thickness of the optic itself, causing the haptic to protrude from the lens surface. In the alternative, the looped anchoring head may be positioned closer to the thicker central optical zone of the lens and away from the thinner lens periphery. Unfortunately, the presence of the anchoring head in the optical zone may distort or detract from the image seen through the lens optic.

Another disadvantage inherent in the welded-loop anchoring head haptic is the potential for the weld to break as the filament is subjected to longitudinal stress. This has been known to result in the haptic pulling away from its anchoring point and out of the optic altogether.

Insofar as the weld itself is concerned, it may be prone to chemical degradation, which may contaminate the ambient environment after implantation. Such an occurrence could be catastrophic in the eye because it may lead to vision problems.

There have been attempts at configuring other shapes for the enlarged anchoring head, aside from welded-loop discussed above. For instance, the attempts of Ting, Knight, as well as those seen in U.S. Pat. No. 4,888,013 to Ting et al. and U.S. Pat. No. 4,978,354 to Van Gent collectively disclose enlarged anchoring heads having a triangular shape, a saw-tooth shape, an arrow-head shape, a knob shape, a barbed hook shape, and a hammer-head shape. The resulting haptics, however, have proven inadequate for a variety of reasons, for instance: (1) reliance on bonds that may fail or chemically leach into the environment; (2) non-adherence of optic/haptic materials; (3) an axially symmetrical anchoring head design that cannot resist torque along that rotational axis; or (4) the anchoring head shapes are too bulky.

A key to superior pull strength is the amount of surface area that the anchoring head engages in a specific direction within the lens optic. Indeed, it determines the pull strength, and the ability of the haptic-optic joint to withstand torsional and bending forces.

Therefore, there is a need for an improved haptic that exhibits high pull strength, and resists torsional and bending forces, yet easily adapts to mass production, and is biocompatible.

SUMMARY OF THE INVENTION

Accordingly, it is an object of the present invention to provide a haptic that has high pull strength along with torsional and bending force resistance at its point of attachment to the lens optic. It is another object of the present invention to provide an improved haptic that is easily adaptable to automated mass production. It is yet another object of the present invention to provide an improved haptic that is biologically inert, and causes little or no trauma to the patient's eye during implantation surgery or thereafter. It is still yet another object of the present invention to provide an improved haptic that includes an enlarged anchoring head to engage a significant amount of lens optic material and is simultaneously thin and unobtrusive.

The present invention provides an intraocular lens haptic having an enlarged anchoring head. The present invention also provides an oblong hole that is disposed in the anchoring head. During fabrication, the lens optic is cast around the enlarged anchoring head and lens optic material flows around the anchoring head and through the oblong hole. Once the casting solidifies, the anchoring head is firmly embedded in the lens optic. With the anchoring head so disposed, there is a significant amount of lens optic material that the anchoring head engages.

In a preferred embodiment, the enlarged anchoring head has a polygonal, preferably rectangular shape. A tail-like support portion of the haptic, formed integrally and simultaneously with the anchoring head extends at a substantially right angle therefrom. In this respect, the point of intersection between the two structures forms a "T" with outstretched shoulders. Beneficially, these outspread shoulders help prevent detachment of the anchoring head from the lens optic when a tensile force is applied along the haptic support portion because of the relatively large expanse of lens optic material obstructing its motion.

The present invention includes another reinforcement means to protect against detachment. As mentioned above, in the preferred embodiment, the lens optic material is cast into the oblong hole during formation of the lens. The lens optic material, in effect, latches the oblong hole and interlocks the two structures together. Once locked in position, the enlarged anchoring head is not easily separated because detachment requires that the anchoring head tear through the lens optic material.

In the preferred embodiment of the present invention haptic, both the anchoring head and the support portion are fabricated in one piece from sheet material. Although it is contemplated as being within the scope of the present invention to cast or etch the haptic, preferably, the haptic is punched out of the sheet of material. Similarly, the oblong hole is created by punching. Because it is derived from sheet form, the haptic is free from the twisting that may appear with circular cross-section support portions in the prior art. Furthermore, no bonds or welds are needed so chemical degredation and leaching are not a problem.

In addition, because the present invention haptic is preferably punched from sheet material, the support portion of the haptic is easily configured into a variety of different shapes that can be customized to ensure stability and centration of the optic. Many of these shapes are not obtainable with conventional haptics because of fabrication problems, thickness problems, springback in the material, welding or bonding problems, etc.

In addition, the present invention haptic is adaptable to mass production. As stated above, the haptic material begins in sheet form, preferably a ribbon. The ribbon is fed to the press area, where it is aligned over a die, and where a punch is lowered thereon. A blank of the haptic silhouette is thus cut out of the ribbon. The stroke of the punch is repeated over and over.

In this manner, large quantities of haptics of whatever size or shape are produced with minimal assistance from skilled human labor. Consequently, production quality can be maintained at a high level, with associated costs remaining relatively low.

Another advantage of the present invention is that, with a sheet haptic, a designer can choose a preferred orientation for the haptic's microscopic grain structure. More specifically, in many cases the grain pattern of the sheet stock is homogeneous and aligned in one direction. So by aligning the sheet in a particular direction during the forming operation, it is possible to cause the grains to run a certain way along the haptic blank. As is known in the art, grain orientation has an influence on material strength. In the preferred embodiment, the grain structure is lined up along the long dimension of the haptic.

DETAILED DESCRIPTION OF THE INVENTION

The following specification describes an improved intraocular lens haptic. In the description, specific materials and configurations are set forth in order to provide a more complete understanding of the present invention. But it is understood by those skilled in the art that the present invention can be practiced without those specific details. In some instances, well-known elements are not described precisely so as not to obscure the invention.

Generally, the present invention is directed to an intraocular lens haptic having an enlarged anchoring head with an oblong hole therethrough, and an integrally formed support portion. By virtue of its enlarged anchoring head and integrally formed support structure, the present invention haptic exhibits high pull strength, and resists torsional forces and bending forces applied to the support structure. As a result, the haptic is highly resistant to detachment from the lens optic.

Figure 1:
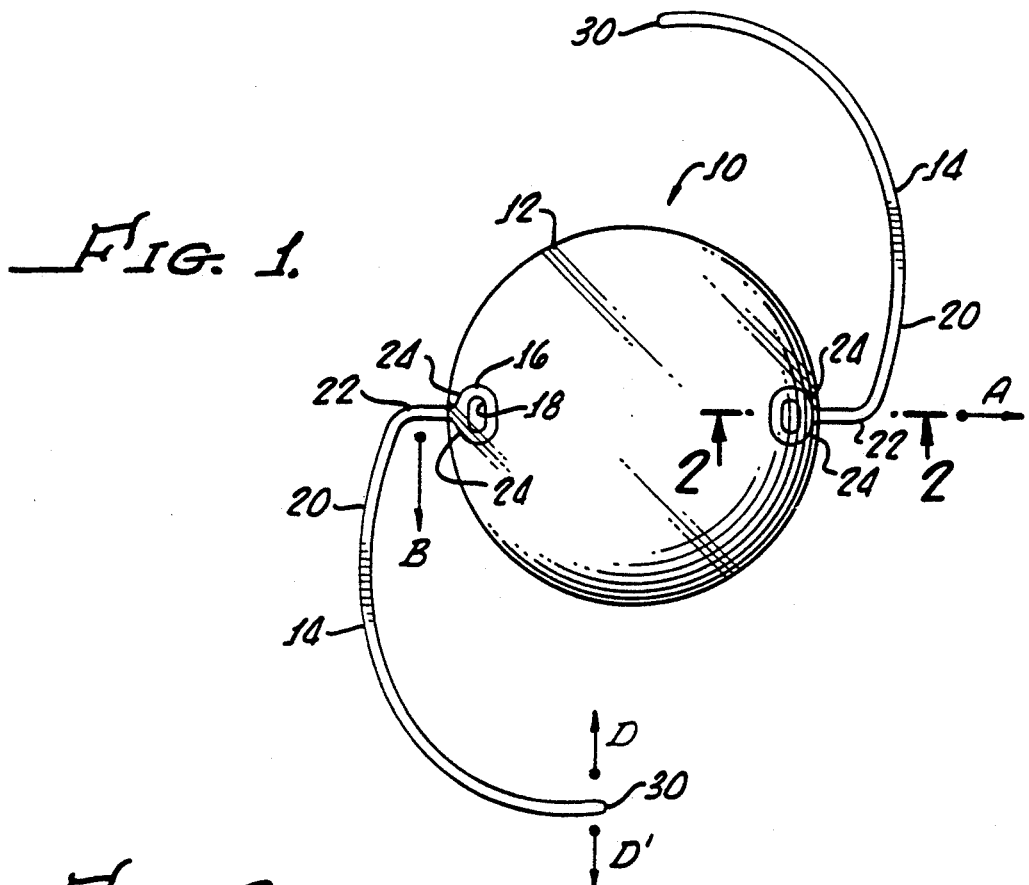
FIG. 1 is a plan view of an exemplary embodiment of the present invention intraocular lens showing preferred embodiment haptics.
Figure 2:
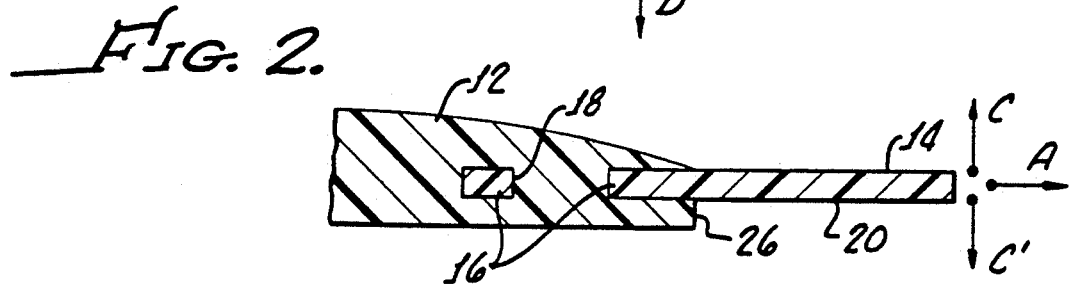
FIG. 2 is a cross-sectional view of a preferred embodiment anchoring head taken along line 2—2 of FIG. 1.

FIG. 1 provides a plan view of a preferred embodiment intraocular lens 10. The intraocular lens 10 includes a lens optic 12 and identical lens haptics 14 disposed on generally diametrically opposed positions along the lens optic outer periphery 26 as shown in FIG. 2. In the preferred embodiment, the two lens haptics 14 are identical; but naturally, non-identical haptics can be paired for use in an alternative embodiment when necessary.

Also in the preferred embodiment, the present invention haptic 14 is punched out of a thin sheet of material. An oblong hole 18 is provided in the anchoring head 16 of the haptic 14. Preferably, the oblong hole 18 defines a long dimension of from 0.4 mm to 0.6 mm, and a short dimension of from 0.2 mm to 0.4 mm. The oblong hole 18 can be punched at any stage of the process as determined by expediency. Further, the haptic 14 and oblong hole 18 can optionally be etched or laser cut out of sheet stock.

The haptic 14 is then placed in a fixture where the lens optic 12 is cast around it. The lens optic material can be a silicone, hydrogel, or polyurethane, or any like material known in the art. During the casting process, lens optic material flows around and completely envelopes the anchoring head 16.

Joined to the anchoring head 16 at a substantially right angle is the support structure 20. Together, the anchoring head 16 and the support structure 20 form the lens haptic 14.

Unlike prior art haptics, the anchoring head 16 and the support structure 20 of the present invention haptic 14 are fashioned as a single, integral piece during the forming operation. No welding, bonding, or other fastening operations are necessary to hold the anchoring head 16 to the support structure 20. Nor is any such fastening operation needed for the anchoring head 16 to retain its shape or to stay embedded within the confines of the lens optic 12 after the casting operation.

Also, because the present invention haptic is preferrably punched from a single sheet, it is possible to align the grain orientation of the material in a particular direction. As long as the grain pattern in the sheet stock is uniform, it can be passed under the punch in a variety of orientations to yield punched haptics with their grain structures aligned in the corresponding directions. Grain orientation of the material is important, as is known in the art, because it has an influence on structural strength.

It is worthwhile to note the large area occupied by the anchoring head 16, as shown in FIG. 1. The importance is that if a force were applied to the haptic 14 as indicated by arrow A in FIG. 1, the outspread shoulders 24 of the anchoring head 16 would encounter the lens haptic material that had flowed therearound during the casting process. Accordingly, the material around the shoulders 24 would prevent the outward tensile force acting along A from pulling the anchoring head 16 out of engagement with the lens optic 12. This is a problem that may occur during surgery with prior art haptics.

FIG. 2 is a cross-sectional view of the lens optic 12 and anchoring head 16 taken along line 2—2 of FIG. 1. As shown in the drawing and as mentioned above, the lens optic 12 is cast around the anchoring head 16, and lens optic material has solidified inside the oblong hole 18. In fact, the anchoring head 16 is effectively embedded into the lens optic 12. Thus, detachment can occur only if a tensile force acting along direction A pulling outward radially is large enough to drag the anchoring head 16 through the lens optic material that has formed around it. In short, the tensile force acting on the anchoring head 16 must be severe enough to cause failure in the lens optic material disposed therearound.

The present invention provides another strength reinforcement feature in the anchoring head 16. Specifically, the asymmetrical or non-circular shape of oblong hole 18 assures that there is sufficient contact between the interior of the oblong hole 18 with the lens optic material along a direction indicated by arrow B. Therefore, more lens optic material is engaged when a force pulls along the A direction when the oblong hole 18 has an oblong shape rather than, for example, a circular shape. The stress caused by a force in the A direction is spread over a larger cross-sectional area for an oblong hole as compared to a circular hole, because that area has a larger dimension in the B direction in the former than in the latter, assuming a common height dimension.

Should a force be applied in the direction of C or C' as shown in FIG. 2 to the support portion 20, the anchoring head 16 and surrounding structures would experience bending moments as well as torques. Advantageously, the present invention provides an enlarged anchoring head 16 designed to be disposed within the plane of the lens optic 12 or at a slight angle thereto. From the vantage point of FIG. 1, it is clear that the anchoring head 16, despite the oblong hole 18, still occupies a large surface area. As a result, there is sufficient contact between the anchoring head 16 and the lens optic 12 to withstand or resist such bending or torsional forces and thereby maintain the structural integrity of lens 10 during implantation.

Furthermore, the area moment of inertia of the anchoring head 16 is relatively large because its asymmetrical shape places large areas of the anchoring head 16 away from a typical axis of rotation, here axis A. The need for a relatively large area moment of inertia is clear when one recognizes that the support structure is a large lever arm and any forces applied at end 30, for example, would generate large bending moments and torques at the anchoring head 16.

In addition, the asymmetrically-shaped oblong hole 18 serves another purpose. Specifically, if a force were applied along a direction indicated by arrow D or D', the anchoring head 16 would then experience a torque tending to twist the head 16 out of engagement with the lens optic 12. However, the asymmetrical shape of the oblong hole 18, which as mentioned above contains material integrally formed with the lens optic 12, resists that torsional force. To, be sure, the oblong shape of the lens optic material in the oblong hole 18 meshes with this hole so that any rotation therebetween the anchoring head 16 and lens optic 12 is obstructed. The force applied along direction D or D' must be so great that it causes the lens optic material disposed in the oblong hole 18 to fail before detachment of the anchoring head 16 from the lens optic 12 can occur.

Notably, as shown in FIG. 2, the lens haptic 14 and the lens optic 12 are formed into a relatively planar arrangement. Of course, the relative disposition between the lens haptic 14 and the lens optic 12 can be altered if necessary so that one is angled relative to the other. Moreover, the lens optic 12 may even have a concave-convex or cupped shape and still be easily integrated with the present invention haptic 14.

Staying with FIG. 2, one observes that the haptic 14 has a preferably uniform cross-section. The anchoring head 16 is thin like the support portion 20 and does not encroach into a third dimension, defined by arrow C or C'. Unlike prior art filament haptics that form the anchoring head by curling the filament around and doubling up the material for welding, the present invention is sleek or of a uniform thickness throughout. Consequently, the present invention haptic is thin enough to be installed at an outer periphery 26 of the lens optic where thicknesses may range only from 0.1 to 0.3 mm. By contrast, prior art haptics that have doubled up anchoring heads must be installed more toward the center optical zone of the lens optic in order to accommodate the obtuse thickness of the doubled up anchoring head. Needless to say, that sort of bulkiness detracts from the quality of the vision provided by the intraocular lens.

FIG. 1 provides a good plan view of the intraocular lens 10 to show the general shape of the preferred embodiment haptic 14. As discussed above, the lens haptic 14 has an anchoring head 16 having a generally polygonal or rectangular shape with rounded corners. Of course, the anchoring head in alternative embodiments can have sharp corners; even the overall polygonal shape of the anchoring head can be replaced by an arcuate shape such as an ellipse and the like.

Similarly, the oblong hole 18 can, in alternative embodiments, be modified to have various shapes. The important aspect of the oblong hole 18 is that it remain asymmetrical, being generally defined by a long diameter or dimension and a short diameter or dimension, wherein the former is perpendicular to the latter. In the preferred embodiment, the oblong hole has an aspect ratio of long diameter to short diameter of about 3 to 1.

In the preferred embodiment, the support portion 20 extends perpendicularly from the anchoring head 16, thereby forming a substantially right angle at the point of intersection between the two structures. As mentioned earlier, in the preferred embodiment, the anchoring head 16 and the haptic 14 are fabricated from a single sheet of material. Consequently, the present invention haptic avoids the numerous problems seen in prior art haptics wherein welds, bonded joints, and other failure prone connections are necessary. It is clear, however, that the intersection between the anchoring head 16 and the haptic 14 can deviate from a right angle if needed for a particular application. In their perpendicular orientation, however, the right angle intersection is advantageous in that any pull-out forces are spread along direction A and consequently, the shoulders 24 of the anchoring head 16 are squared to directly oppose the pull-out force. Hence, the utility of having a right angle intersection is understood.

Between the anchoring head 16 and the end 30 of the haptic 14 is an intermediate portion. In this intermediate portion, in the preferred embodiment, is a bend 22. The bend 22 is preferred to position the support portion 20 for proper implantation in the bag inside the eye. Because the bend 22 is formed simultaneously with the entire haptic 14 as the latter is punched out, there is no tendency for the bend 22 to spring back to, for instance, an unbent formation. In comparison, a conventional filament haptic that is bent to shape may exhibit spring back after a period of use. Furthermore, the bend or crimp in a filament imparts stress raisers in the bend that might eventually lead to a failure. In any event, the present invention haptic 14 can be modified to have a bend 22 that defines a variety of angles as determined by the specific application.

As stated in the beginning, in the preferred embodiment of the present invention, the haptic 14 may be punched from a sheet of polyvinylidene fluoride film. The material is commonly known in the industry as KYNAR ™, available from Westlake Plastic Company, Lenni, Pa. This material is chemically inert, is biocompatible, and when fashioned into a haptic, exhibits sufficient strength to ensure centration and stable positioning of the lens optic. The haptic may also be made from polyamide, polyimide, polymethylmethacrylate, polytetrafluoroethylene (commonly known as Teflon), polypropylene, polycarbonate, polyurethane, or other suitable biocompatible materials.

TABLE 1 provides a comparative analysis illustrating the high pull strengths available with an exemplary haptic of the present invention. It tabulates the average tensile force applied to a haptic before it detaches from the lens optic for a variety of haptic configurations.

The experiment was conducted using five haptic variations, listed in the left-most, first column of TABLE 1. The experiment was conducted by applying a radial, outward, tensile force on the haptic, urging the haptic to detach from the lens optic. All test lenses were made using the same mold and silicone formula for the lens optic and all haptics were formed of Kynar 740. The force required for detachment was calculated in grams, with the average of ten lenses shown in the right-most column. The second and third columns list the range from the minimum force required for detachment to the maximum force needed for detachment for each configuration.

TABLE 1

| Haptic Tensil Force/Pull Strength | | | | |
|---|---|---|---|---|
| Haptic Head Shape | Minimum | Maximum | Standard Deviation | Average 10 Lenses |
| Prior Art Monofilament .3 mm Round Eyelet | 18 | 73 | 17.264 | 46.80 |
| Prior Art 'T' Type Design | 29 | 96 | 29.716 | 59.11 |
| Prior Art Punched Film | 23 | 44 | 6.434 | 31.65 |
| .3 × .5 mm Eyelet No Hole | | | | |
| .3 × .5 mm Eyelet Small Hole | 44 | 71 | 5.913 | 55.70 |
| .3 × .5 mm Eyelet | 48 | 70 | 6.407 | 59.00 |

TABLE 1-continued

| | Haptic Tensil Force/Pull Strength | | | |
|---|---|---|---|---|
| Haptic Head Shape | Minimum | Maximum | Standard Deviation | Average 10 Lenses |
| Large Hole | | | | |

As shown in TABLE 1, haptics configured with the anchoring head configurations of the present invention exhibited the highest average pull strengths in combination with the lowest standard deviation relative to the pull strengths of the three prior art head shape configurations. More specifically, though the prior art "T" type design exhibited the highest average pull strength of 59.11 grams, it also had the highest standard deviation of 26.716. Similarly, though the prior art anchoring head no hole design exhibited a low standard deviation of 6.434 it also exhibited the lowest average pull strength of 31.65 grams. Similarly, the prior art monofilament anchoring head design exhibited a high standard deviation of 17.264 and a moderate average pull strength of 46.80 grams.

In contrast, the preferred large hole anchoring head design of the present invention exhibited a high average pull strength of 59.00 grams with a low standard deviation of 6.407. Similarly, an alternative embodiment small hole anchoring head design of the present invention exhibited an average pull strength of 55.70 grams with the lowest standard deviation of 5.913.

Thus, it is clear from the foregoing that the various haptic configurations of the present invention exhibit higher pull strengths with a much narrower statistical bell curve, implying that these elevated pull strengths can be maintained from one lens to the next. As those skilled in the art will appreciate, this is a critical feature to repeatable lens quality during mass production. Moreover, these beneficial pull strengths were obtained by virtue of the relative haptic head shape configurations as opposed to the haptic materials as identical materials were used throughout. Accordingly, these benefits can be achieved utilizing other haptic formation materials. For example, in other alternative embodiments, the haptic can be punched from a variety of materials including fiber reinforced sheets, laminated sheet material, or the like. For the convenience of the surgeon, the haptic may also have a color so that it can be seen easily.

Figures 3, 4:
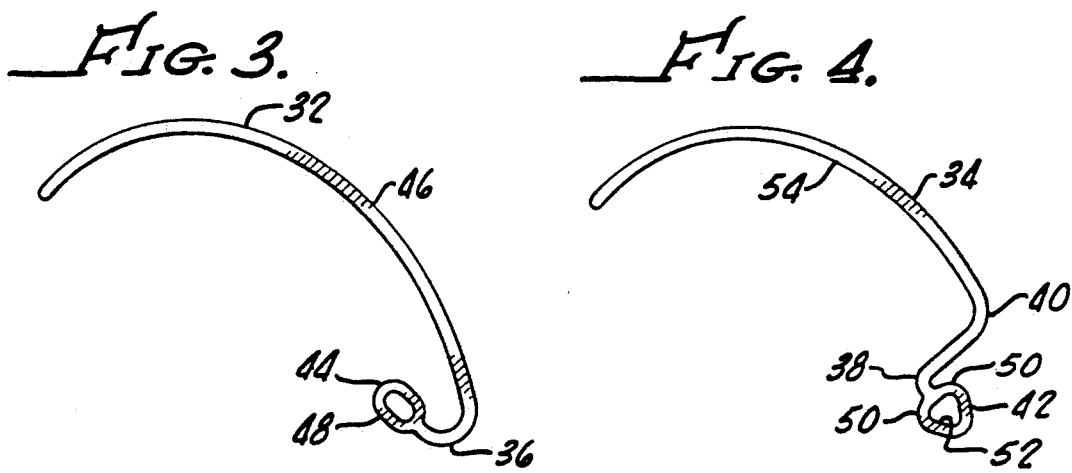
FIG. 3 illustrates an alternative embodiment of the present invention haptic.
FIG. 4 illustrates another alternative embodiment of the present invention haptic.

FIG. 3 provides a plan view of an alternative embodiment haptic 32. In this embodiment, the anchoring head 44 is attached to support portion 46 via hairpin bend 36. When installed in a lens optic, the support portion 46 wraps sharply around the outer circumference of the lens optic. Furthermore, note that the orientation of the anchoring head 44 and the oblong hole 48 have been uniformly shifted so that the direction of the asymmetry is different than the orientation shown in FIG. 1. That is, the long diameter or dimension has been rotated approximately 90 degrees. Naturally, the long diameter or dimension of the oblong hole can be disposed in almost any orientation relative to the support portion depending upon specific application.

FIG. 4 illustrates yet another alternative embodiment in which the anchoring head 42 has a generally triangular shape with hooks 50 positioned at two vertices. It is clear that the hooks 50 are present to help latch onto the lens optic material once the anchoring head 42 is embedded therein.

Another feature of this embodiment is that the support portion 54 of the haptic 34 features two bends 38 and 40. As mentioned above, an advantage of the present invention is that it may be fabricated from a punching operation. Therefore, it is easy to impart bends into the support portion 54 at any location and in any number necessary.

Although the present invention has been described in connection with the preferred embodiments, it is evident that numerous alternatives, modifications, variations, and uses will be apparent to those skilled in the art in light of the foregoing description. Therefore, the scope of the present application should not be limited to those aforementioned embodiments.

What is claimed is:

1. An intraocular lens comprising:
   a lens optic;
   at least one haptic including an elongate support portion and an enlarged integral anchoring head of a single materially uniform piece therewith, said anchoring head being disposed in the intraocular lens optic and including an oblong hole; and
   wherein the anchoring head and the support portion are everywhere of substantially the same thickness and are disposed in a generally planar arrangement.

2. An intraocular lens according to claim 1, wherein said anchoring head is generally polygonal with a long dimension, and the support portion and the anchoring head of the haptic at the intersection thereof define a substantially right angle therebetween relative to the direction of said long dimension, and the support portion extends generally along a radial direction along the intraocular lens optic for at least a portion of the length of the haptic.

3. An intraocular lens according to claim 2, wherein the anchoring head and the support portion have a substantially uniform thickness.

4. An intraocular lens according to claim 3, wherein the oblong hole further comprises a long diameter and a short diameter, and the anchoring head is disposed in the intraocular lens optic so that the long diameter is oriented in other than along a radial direction of the intraocular lens optic.

5. An intraocular lens according to claim 4, wherein an aspect ratio of the long diameter relative to the short diameter is at least 3 to 1.

6. An intraocular lens according to claim 5, wherein the haptic includes a grain structure generally aligned with a length of an elongate section of the support portion.

7. An intraocular lens according to claim 5, wherein the haptic is made from a material selected from the group consisting of polyvinylidene fluoride, polyamide, polyimide, polymethylmethacrylate, polytetrafluoroethylene, polypropylene, polycarbonate, and polyurethane.

8. An intraocular lens according to claim 5, wherein the intraocular lens optic is made from a material selected from the group consisting of silicone, hydrogel, and polyurethane.

9. An intraocular lens according to claim 5, wherein the support portion includes a substantially right angle bend at an intermediate portion thereof between the anchoring head and the opposite end of said support portion.

10. An intraocular lens according to claim 5, wherein the anchoring head is a polygonal shape.

11. An intraocular lens according to claim 4, wherein the long diameter is from about 0.4 to 0.6 mm and the short diameter is from about 0.2 to 0.4 mm.

12. An intraocular lens haptic comprising:
a polygonal anchoring head defining a substantially oblong hole therethrough;
a support portion integral and of a single materially uniform piece with the anchoring head and disposed in a substantially planar arrangement therewith, said haptic being of substantially uniform thickness; and
said anchoring head being substantially enlarged in plan view size relative to said support portion.

13. An intraocular lens haptic according to claim 12, wherein the anchoring head and the support portion are integral to define a substantially right angle therebetween at the intersection of said support portion with said anchoring head and with respect to a longer dimension of said oblong hole.

14. An intraocular lens haptic according to claim 13, wherein the anchoring head and the support portion have a substantially uniform thickness.

15. An intraocular lens haptic according to claim 14, wherein the haptic is made from a material selected from the group consisting of polyvinylidene fluoride, polyamide, polyimide, polymethylmethacrylate, polytetrafluoroethylene, polypropylene, polycarbonate, and polyurethane.

16. An intraocular lens comprising:
a circular intraocular lens optic; and
a haptic of polyvinylidene fluoride sheet material having substantially planar opposite faces which are generally parallel to define a substantially uniform thickness for said haptic, said haptic further being free of welds or bonds therein, and said haptic including:
an anchoring head having a polygonal shape, said anchoring head being embedded at an outer periphery of the intraocular lens optic, said anchoring head including an oblong hole; and
a support portion, integral with the anchoring head to at the intersection with the latter define a substantially right angle with respect to a longer dimension of said oblong hole, wherein the anchoring head and the support portion are disposed in a generally planar arrangement, and the support portion extends in a radial direction relative to the intraocular lens optic, and wherein the support portion further includes a substantially right angle bend at an intermediate portion of the support portion;
whereby the polygonal shape and oblong hole of the anchoring head engage a predetermined area of material of the intraocular lens optic to resist torque, tension, and bending, thereby maintaining engagement between the anchoring head and the support portion.

17. A flexible intraocular lens comprising:
a lens optic portion of flexible shape-retaining material, said lens optic defining a plane;
at least one haptic portion of a single piece including an elongate support structure section at one end thereof having an integral anchoring head section, said anchoring head section in plan view of said intraocular lens being enlarged relative to said support section and of non-circular shape to define a side edge, said support structure section intersecting with said side edge at an angle of substantially ninety degrees to that on each side of said intersection the anchoring head section defines a shoulder, said anchoring head section further defining a non-circular hole extending therethrough in a direction substantially perpendicular to said plane, and said haptic portion also being everywhere of substantially the same thickness in said direction;
said haptic portion at said anchoring head section thereof being embedded into a peripheral part of said lens optic portion with said support section extending outwardly therefrom generally in said plane, and said lens optic portion surrounding said non-circular anchoring head section and extending through said non-circular hole therein to capture said anchoring head section substantially immovably within said lens optic portion.

18. The intraocular lens of claim 17 wherein said enlarged anchoring head section is of polygonal shape in plan view.

19. The intraocular lens of claim 17 wherein said non-circular hole is of oblong shape and includes a larger dimension and a smaller dimension.

20. The intraocular lens of claim 19 wherein said hole defines an aspect ratio of said larger dimension to said smaller dimension, said aspect ratio being at least three-to-one.

21. The intraocular lens of claim 19 wherein said hole defines a larger dimension in the range of from 0.4 mm to 0.6 mm, and a smaller dimension in the range of from 0.2 mm to 0.4 mm.

22. The intraocular lens of claim 17 wherein said lens optic portion at said peripheral part thereof has a thickness in said direction of from 0.1 mm to 0.3 mm, said haptic portion everywhere having a thickness less than that of said lens optic portion at said peripheral part thereof.

* * * * *